United States Patent
Loori et al.

(10) Patent No.: US 9,174,034 B2
(45) Date of Patent: Nov. 3, 2015

(54) ADAPTABLE TOPICAL HYPERBARIC DEVICE

(75) Inventors: Phillip Loori, Farmingdale, NJ (US); George Hovorka, East Boston, MA (US)

(73) Assignee: AOTI, Inc., Oceanside, CA (US)

( * ) Notice: Subject to any disclaimer, the term of this patent is extended or adjusted under 35 U.S.C. 154(b) by 684 days.

(21) Appl. No.: 12/291,317

(22) Filed: Nov. 6, 2008

(65) Prior Publication Data
US 2009/0143751 A1 Jun. 4, 2009

Related U.S. Application Data (60) Provisional application No. 61/001,966, filed on Nov. 6, 2007.

(51) Int. Cl.
| | |
|---|---|
| *A61M 35/00* | (2006.01) |
| *A61M 37/00* | (2006.01) |
| *A61F 13/00* | (2006.01) |
| *A61G 10/00* | (2006.01) |
| *A61B 7/00* | (2006.01) |

(52) U.S. Cl.
CPC ........... *A61M 35/00* (2013.01); *Y10T 29/49826* (2015.01)

(58) Field of Classification Search
CPC ....... A61M 37/00; A61M 35/00; A61F 13/00; A61G 10/00; A61B 7/00
USPC .................................. 604/23, 289, 305, 308
See application file for complete search history.

(56) References Cited

U.S. PATENT DOCUMENTS

| | | |
|---|---|---|
| 871,760 A | 11/1907 | Long et al. |
| 1,117,168 A | 11/1914 | Crowley |
| 2,134,646 A | 10/1938 | Sauzedde |
| 3,368,556 A | 2/1968 | Jensen et al. |
| 3,478,738 A | 11/1969 | Altman et al. |
| 3,602,221 A | 8/1971 | Bleicken |
| 3,604,421 A | 9/1971 | Pizzella |
| 3,669,096 A | 6/1972 | Hurwitz |
| 3,701,349 A | 10/1972 | Larson |
| 3,712,298 A | 1/1973 | Snowdon et al. |
| 3,744,491 A | 7/1973 | Fischer |
| 3,785,374 A | 1/1974 | Lipson |
| 3,920,006 A | 11/1975 | Lapidus |

(Continued)

FOREIGN PATENT DOCUMENTS

| | | |
|---|---|---|
| DE | 19846922 A1 | 4/2000 |
| EP | 0392669 A2 | 10/1990 |

(Continued)

OTHER PUBLICATIONS

U.S. Appl. No. 12/291,338, filed Nov. 8, 2008.

(Continued)

*Primary Examiner* — Tatyana Zalukaeva
*Assistant Examiner* — Ilya Treyger
(74) *Attorney, Agent, or Firm* — Lerner, David, Littenberg, Krumholz & Mentlik, LLP (57) ABSTRACT

A wound treatment device includes a seal of variable size for attaching the device to various locations on a patient for treatment of wounds or lesions. The seal has a plurality of weakened areas which allow portions of the seal to be removed for increasing the size of the seal opening to accommodate wounds or lesions of different size.

9 Claims, 8 Drawing Sheets

(56) References Cited

U.S. PATENT DOCUMENTS

| | | | |
|---|---|---|---|
| 3,955,565 A | 5/1976 | Johnson, Jr. | |
| 4,003,371 A | 1/1977 | Fischer | |
| 4,211,223 A | 7/1980 | LoPiano | |
| 4,227,524 A | 10/1980 | Galerne | |
| 4,236,513 A | 12/1980 | LoPiano | |
| 4,280,489 A | 7/1981 | Johnson, Jr. | |
| 4,328,799 A | 5/1982 | LoPiano | |
| 4,331,133 A | 5/1982 | Arkans | |
| 4,346,699 A | 8/1982 | Little et al. | |
| 4,353,359 A | 10/1982 | Milbauer | |
| 4,363,317 A | 12/1982 | Broucek | |
| 4,378,009 A | 3/1983 | Rowley et al. | |
| 4,460,370 A | 7/1984 | Allison et al. | |
| 4,628,945 A | 12/1986 | Johnson, Jr. | |
| 4,633,859 A | 1/1987 | Reneau | |
| 4,635,635 A | 1/1987 | Robinette-Lehman | |
| 4,667,672 A | 5/1987 | Romanowski | |
| 4,801,291 A | 1/1989 | Loori | |
| 5,000,164 A | 3/1991 | Cooper | |
| 5,007,411 A | 4/1991 | Dye | |
| 5,029,579 A | 7/1991 | Trammell | |
| 5,060,644 A | 10/1991 | Loori | |
| 5,125,400 A | 6/1992 | Johnson, Jr. | |
| 5,154,697 A | 10/1992 | Loori | |
| 5,211,642 A | 5/1993 | Clendenning | |
| 5,234,459 A | 8/1993 | Lee | |
| 5,264,218 A | 11/1993 | Rogozinski | |
| 5,312,385 A | 5/1994 | Greco | |
| 5,376,067 A | 12/1994 | Daneshvar | |
| 5,437,602 A | 8/1995 | Polyakov et al. | |
| 5,458,562 A | 10/1995 | Cooper | |
| 5,478,310 A | 12/1995 | Dyson-Cantwell et al. | |
| 5,578,055 A | 11/1996 | McEwen | |
| 5,605,534 A | 2/1997 | Hutchison | |
| 5,620,001 A | 4/1997 | Byrd et al. | |
| 5,660,182 A | 8/1997 | Kuroshaki et al. | |
| 5,669,390 A | 9/1997 | McCormick et al. | |
| 5,678,543 A | 10/1997 | Bower | |
| 5,688,236 A | 11/1997 | Gragg | |
| 5,738,093 A | 4/1998 | Santi | |
| 5,810,795 A | 9/1998 | Westwood | |
| 5,865,722 A | 2/1999 | Heng | |
| 6,007,559 A | 12/1999 | Arkans | |
| 6,120,860 A | 9/2000 | Bowen et al. | |
| 6,235,365 B1 | 5/2001 | Schaughency et al. | |
| 6,321,746 B1 | 11/2001 | Schneider et al. | |
| 6,622,326 B2 | 9/2003 | Richardson | |
| 6,702,794 B2 | 3/2004 | Blum et al. | |
| 6,793,644 B2 | 9/2004 | Stenzler | |
| 6,814,720 B2 * | 11/2004 | Olsen et al. ............... | 604/339 |
| 6,881,929 B2 | 4/2005 | Hovorka | |
| 7,998,125 B2 | 8/2011 | Weston | |
| 2003/0036771 A1 | 2/2003 | McEwen et al. | |
| 2005/0161039 A1 | 7/2005 | Gurnee et al. | |
| 2005/0191372 A1 | 9/2005 | Stenzler et al. | |
| 2005/0261615 A1 | 11/2005 | Weston | |
| 2006/0069357 A1 | 3/2006 | Marasco | |
| 2006/0185670 A1 | 8/2006 | Loori et al. | |
| 2007/0037472 A1 | 2/2007 | Greenwald et al. | |
| 2007/0118096 A1 | 5/2007 | Smith et al. | |
| 2008/0140029 A1 | 6/2008 | Smith et al. | |

FOREIGN PATENT DOCUMENTS

| | | |
|---|---|---|
| JP | 45-022313 | 7/1970 |
| JP | 57-195468 | 12/1982 |
| JP | 11-057007 | 3/1999 |
| JP | 2008531113 A | 8/2008 |
| WO | 2008130689 A1 | 10/2008 |

OTHER PUBLICATIONS

The Topical Hyperbaric Oxygen Extremity Chamber.
The Disposable Sacral Topical Hyperbaric Oxygen System.
Heng, et al. "Angiogenesis in Necrotic Ulcers Treated with Hyperbaric Oxygen" OstomyWound Management, Sep. 2000, vol. 46, Issue 9, pp. 18-32.
Edsberg, et al. "Use of Topical Hperbaric Oxygen for Treatment of Chronic Wounds in Long-Termn Health Care Facilities." Natural & Health Sciences Research Center, Daemen College, Amherst, NY.
Edsberg, et al. "Reducing Epibole Using Topical Hyerpbaric Oxygen and Electrical Stimulation" OstomyWound Management Apr. 2002, vol. 48, Issue 4, pp. 26-29.
Diamond, et al. "The Effect of Hyperbaric Oxygen on Lower Extremity Ulcerations" Journal of the American Podiatry Association, vol. 72, No. 4, Apr. 1982, pp. 180-185.
Lehman, et al. "Human Bite Infections of the Hand: Adjunct Treatment with Hyperbaric Oxygen" Orthopedic Complications, Infections in Surgery, Jun. 1985, pp. 460-465.
Fischer "Topical Hyperbaric Oxygen Treatment of Pressure Sores and Skin Ulcers" reprinted from The Lancet, Aug. 23, 1969, pp. 405-409.
Upson "Topical Hyperbaric Oxygenation in the Treatment of Recalcitrant Open Wounds—A clinical report" Physical Therapy, vol. 66, No. 9, Sep. 1986, pp. 1408-1411.
Fischer "Treatment of Ulcers on the Legs with Hyperbaric Oxygen" reprinted from the Journal of Dermatologic Surgery, Inc. vol. 1, No. 3, Oct. 1975, J of Derm Surg 1:3, Oct. 1975, pp. 55-58.
Heng "Topical Hyperbaric Therapy for Problem Skin Wounds" J Dermatol Surg Oncol. Aug. 1993; 19(8):784-93, Department of Medicine, UCLA San Fernando Valley Internal Medicine Program, Veterans Administration Medical Center, Sepulveda, PMID: 8349920 [PubMed—indexed for Medline].
Kalliainen, et al. "Topical oxygen as an adjunct to wound healing: a clinical case series" ISP Pathophysiology 9 (2003) 81-87, 2002 Elsevier Science Ireland Ltd.
Kaufman, et al., "Topical oxygen and burn wound healing: a review" Shriners Burns Institute, Cincinnati Unit, Ohio.
Olejniczak, et al. "Topical Oxygen Promotes Healing of Leg Ulcers" Dec. 1976, Medical Times, vol. 104, No. 12, pp. 115-120.
Fries, et al., "Dermal excisional wound healing in pigs following treatment with topically applied pure oxygen" Mutat. Res. Nov. 11, 2005; 579(1-2): 172-81 Epub Aug. 18, 2005, Laboratory of Molecular Medicine, Dorothy M. Davis Heart and Lung Research Institute and Comprehensive Wound Center, Department of Surgery, The Ohio State University Medical Center, Columbus, OH, PMID: 16105672 [PubMed—in process].
Stryker-Taoti Advanced Oxygen Therapy, Inc. Wound Care Solution Excellence, Strategic Discussions Kalamazoo, Michigan, Mar. 21, 2007 powerpoint presentation, 96 pages.
Clinical Device Group and the Food and Drug and Law Institute are happy to present: "Getting CMS Reimbursement for Medical Technology Product" 2006, Clinical Device Group, Inc. Powerpoint presentation, 78 pages.
Medical Coverage Advisory Committee, Usual Care of Chronic Wounds, Powerpoint presentation, 144 pages.
CDC Diabetes, Department of Health and Human Services, Centers for Disease Control and Prevention, "National Diabetes Fact Sheet", United States, 2003, General Information, 3 pages.
Pompeo "The Role of "Wound Burden" in Determining the Costs associated with Wound Care" OstonomyWound Management, Mar. 2001, vol. 47, Issue 3, pp. 65-71.
Frykberg, et al. "Diabetic Foot Disorders: A Clinical Practice Guideline" 2006 revision, The Journal of Foot and Ankle Surgery, vol. 45, No. 5, Sep./Oct. 2006, S1-S66.
American Diabetes Association, "Economic Costs of Diabetes in the U.S. in 2002" Diabetes Care, vol. 26, No. 3, Mar. 2003, pp. 917-932.
Snyder, et al. OstomyWound—Osteomyelitis in the Diabetic Patient: Overview, Diagnosis, Microbiology, "Osteomyelitis in the Diabetic Patient: Diagnosis and Treatment Part 1: Overview, Diagnosis, and Microbiology" (Abstract).
Branom, et al., "'Constant Force Technology' versus Low-Air-Loss Therapy in the Treatment of Pressure Ulcers", OstomyWound—Utilizing a Systems Approach to Implement Pressure Ulcer Prediction and Prevention, Sep. 2001, vol. 47, Issue 9, pp. 38-39.
Landau, et al. "Topical hyperbaric oxygen and low energy laser therapy for chronic diabetic foot ulcers resistant to conventional treatment" Yale J. Biol. Med. Mar.-Apr. 2001; 74(2):95-100, The (56) References Cited

OTHER PUBLICATIONS

Hebrew University, Hadassah School of Medicine, Jerusalem, Israel. PMID: 11393266 [PubMed—indexed for Medline].
Sen, et al. "Oxygen, oxidants, and antioxidants in would healing: an emerging paradigm" Laboratory of Molecular Medicine, Dorothy M. Davis Heart and Lung Research Institute, Department of Surgery (CMIS), The Ohio State University Medical Center, Columbus, OH, Ann N.Y. Acad. Sci. May 2002; 957:239-49, PMID: 12074976 [PubMed—indexed for Medline].
Gordillo, et al. "Revisiting the essential role of oxygen in wound healing" Department of Surgery, Laboratory of Molecular Medicine, 512 Davis Heart and Lung Research Institute, The Ohio State University, 473 West 12th Ave., Columbus, OH, Am. J. Surg. Sep. 2003;186(3):259-63, PMID: 12946829 [PubMed—indexed for Medline].
Ignacio, et al. "Topical Oxygen Therapy Treatment of Extensive Leg and Foot Ulcers" Journal of the American Podiatric Medical Association, vol. 75, No. 4, Apr. 1985, pp. 196-199.
Cianci "Advances in the treatment of the diabetic foot: Is there a role for adjunctive hyperbaric oxygen therapy?" Wound Repair Regen, Jan.-Feb. 2004; 129(1):2-10, Department of Hyperbaric Medicine, Doctors Medical Center, San Pablo, California, PMID: 14974958 [PubMed—indexed for Medline].
Hopf, et al. "Hyperoxia and angiogenesis" Blackwell Synergy: Wound Repair Regen, vol. 13, Issue 6, pp. 558-564: Hyperoxia and angiogenesis (Abstract); Wound Repair and Regeneration vol. 13 Issue 6 p. 558—Nov. 2005; http://www.blackwell-synergy.com/doi/abs/10.1111/j.1524-475X.2005.00078.x(1of 3)Dec. 19, 2006.
Kaufman, et al. "The Microclimate Chamber: The Effect of Continuous Topical Administration of 96% Oxygen and 75% Relative Humidity on the Healing Rate of Experimental Deep Burns" The Journal of Trauma, vol. 23, No. 9, pp. 806-815.
Heng, et al. "Endothelial cell toxicity in leg ulcers treated with topical hyperbaric oxygen" Am. J. Dermatopathol Oct. 1986; 8(5):403-10; MID: 3777378 [PubMed—indexed for Medline].
Heng, et al. "Enhanced Healing and Cost-Effectiveness of Low-Pressure Oxygen Therapy in Healing Necrotic Wounds: A feasibility study of technology transfer" Ostomy/Wound Management 2000; 46(3):52-62; From the Division of Dermatology, Department of Medicine, Department of Veterans Affairs, VAGLAHS (Sepulveda), UCLA San Fernando Valley Program, pp. 52-60.
Harkless, et al. "Seven keys to Treating Chronic Wounds" Diabetes Watch, Podiatry Today, Dec. 2000, pp. 17-19.
Diabetes Care, published by the American Diabetes Association "Study Finds Diabetes Will Double in World by 2030: Predicts Rapid U.S. increase That Greatly Exceeds Prior CDC Projections" lead author Dr. Sarah Wild, Public Health Sciences, University of Edinburgh, 2 pages.
Rossi, Hudson Podiatry Center, Letter.
International Search Report, PCT/US2008/12669, dated Dec. 27, 20008.
International Search Report, PCT/US2008/12625, dated Dec. 22, 2008.
International Search Report, PCT/US08/12535, dated Dec. 25, 2008.
U.S. Appl. No. 61/002,269, filed Nov. 7, 2007, entitled "Pressure Compensating Seal With Positive Feedback".
U.S. Appl. No. 11/064,581, filed Feb. 24, 2005, entitled "Hyperbaric Oxygen Device and Delivery methods".
U.S. Appl. No. 12/156,465, filed May 30, 2008, entitled "Controller for an Extremity Hyperbaric Chamber".
U.S. Appl. No. 12/156,466, filed May 30, 2008, entitled "Controller for an Extremity Hyperbaric Chamber".
U.S. Appl. No. 12/291,317, filed Nov. 6, 2008.
U.S. Appl. No. 12/291,348, filed Nov. 7, 2008.
U.S. Appl. No. 12/291,328, filed Nov. 6, 2008.
U.S. Appl. No. 12/291,342, filed Nov. 8, 2008.
U.S. Appl. No. 12/291,347, filed Nov. 8, 2008.
Diabetes Care, published by the American Diabetes Association "Study Finds Diabetes Will Double in World by 2030: Predicts Rapid U.S. increase That Greatly Exceeds Prior CDC Projections" lead author Dr. Sarah Wild, Public Health Sciences, University of Edinburgh, 2 pages.
Dutton, et al. "Topical Hyperbaric Oxygen Therapy: A Case Study" Macassa Lodge, Hamilton, Ontario.
Edsberg, et al. "Use of Topical Hperbaric Oxygen for Treatment of Chronic Wounds in Long-Termn Health Care Facilities" Natural & Health Sciences Research Center, Daemen College, Amherst, NY, Copyright 2001.
Extended European Seach Report for Application No. EP08767897 dated Jun. 3, 2014.
Kaufman, et al. "The Microclimate Chamber: The Effect of Continuous Topical Administration of 96% Oxygen and 75% Relative Humidity on the Healing Rate of Experimental Deep Burns" The Journal of Trauma, vol. 23, No. 9, pp. 806-815, 1983.
Kaufman, et al., "Topical oxygen and burn wound healing: a review" Shriners Burns Institute, Cincinnati Unit, Ohio, 2000.
Medical Coverage Advisory Committee, Usual Care of Chronic Wounds, Powerpoint presentation, 144 pages, 2006.
Rossi, Hudson Podiatry Center, Letter, Nov. 1997.
Snyder, et al. OstomyWound—Osteomyelitis in the Diabetic Patient: Overview, Diagnosis, Microbiology, "Osteomyelitis in the Diabetic Patient: Diagnosis and Treatment Part 1: Overview, Diagnosis, and Microbiology" (Abstract), 2000.
The Disposable Sacral Topical Hyperbaric Oxygen System, Copyright 2000.
The Topical Hyperbaric Oxygen Extremity Chamber, Copyright 1998.
Venous Ulcers Appendix I, Evidence Table per FDA Draft Guidance Document, 8 pages.

\* cited by examiner

ADAPTABLE TOPICAL HYPERBARIC DEVICE

CROSS-REFERENCE TO RELATED APPLICATIONS

This application claims the benefit of the filing date of U.S. Provisional Patent Application No. 61/001,966, filed Nov. 6, 2007, entitled "Adaptable Topical Hyperbaric Torso Unit," the disclosure of which is hereby incorporated herein by reference.

BACKGROUND OF THE INVENTION

Hyperbaric chambers are devices which create sealed environments for the application of therapeutic gases to hasten healing of lesions or wounds on a patient's body. As described in U.S. Pat. No. 5,060,644, the disclosure of which is incorporated herein by reference, the introduction of pressurized gas, such as oxygen, into such an encapsulated environment promotes healing of various types of lesions and wounds.

More recently, topical hyperbaric devices have been developed that are secured to the patient's body about a wound. Examples of these devices are described in U.S. Pat. No. 5,154,697 entitled, "Collapsible Topical Hyperbaric Apparatus" and U.S. Pat. No. 4,801,291, entitled, "Portable Topical Hyperbaric Apparatus," which are incorporated by reference herein. However, their application is usually limited to a discrete range of wound sizes due to their construction. Accordingly, it is desired to provide a topical hyperbaric chamber device that offers a greater range of application to accommodate various sizes of wounds.

SUMMARY OF THE INVENTION

In an embodiment of the present invention, a wound treatment device can include an enclosure defining an interior region having an opening in communication with the interior region. The device can further include a seal affixed to the enclosure surrounding the opening having a plurality of weakened regions of increasing size, whereby a portion of the seal can be separated from another portion of the seal along the weakened regions. Additionally, the device can include a fluid inlet in communication with the interior region and a fluid outlet in communication with the interior region.

In another embodiment of the present invention, a wound treatment device can include an enclosure having an opening, and a seal coupled to the enclosure surrounding the opening. The seal can have portions surrounding the opening constructed to be separated from adjacent portions of the seal.

In yet another embodiment of the present invention, a wound treatment device can include an enclosure having a first opening and a seal having a variable size second opening disposed on the enclosure surrounding the first opening. The seal can be adapted to be releasably attached to a patient's skin.

In still another embodiment of the present invention, a wound treatment device can include an enclosure defining an interior region, and a seal overlying the enclosure. The seal and the enclosure can have a plurality of corresponding weakened regions of increasing size, whereby a portion of the seal and the enclosure can be separated from another portion of the seal and the enclosure along the weakened regions to form an opening.

In another embodiment of the present invention, a method of sizing a wound treatment device can include providing an enclosure having a first opening in communication with an interior of the enclosure, providing a variable size seal coupled to the enclosure surrounding the opening, and removing a portion of the seal to form a second opening larger than the first opening in communication with the interior.

In still another embodiment of the present invention, a method of sizing a wound treatment device can include providing an enclosure having an interior, providing a variable size seal coupled to the enclosure, and removing a portion of the seal to form a first opening in communication with the interior.

In yet another embodiment of the present invention, a method of making a wound treatment device can include providing an enclosure having an opening in communication with an interior of the enclosure, providing a seal coupled to the enclosure adjacent the opening, and weakening aligned concentric portions of the seal and the enclosure.

BRIEF DESCRIPTION OF THE DRAWINGS

The various objects, advantages and features of this invention will be more fully apparent from a reading of the following detailed description in conjunction with the accompanying drawings in which like reference numerals refer to like parts, and in which.

DETAILED DESCRIPTION

Figure 1:
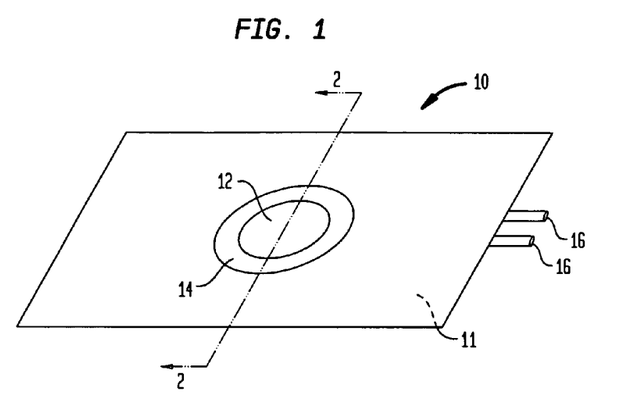
FIG. 1 is a perspective view of a wound treatment device according to an embodiment of the present invention.
Figure 2:
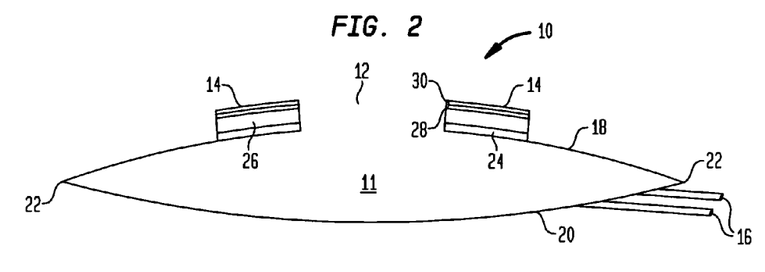
FIG. 2 is a cross sectional view of the device of FIG. 1 taken along line 2-2.

Referring to FIGS. 1 and 2, in an embodiment of the present invention, a hyperbaric wound treatment device 10 includes a customizable flexible and resilient topical hyperbaric wound device that is configured to cover and enclose a wound. The device 10 includes a treatment chamber 11 to apply a treatment gas to the wound enclosed by device 10. As will be more fully described below, device 10 has an opening 12 that is in fluid communication with the treatment chamber 11, faces the patient's body, and is sized to encircle the wound. Opening 12 is configured to accommodate a variety of wound shapes and sizes. Though illustrated with a generally rectangular shape, device 10 may be configured in any desired shape, for example, circular, or oval, or other geometric shapes or a random non-geometric shape. Similarly, while opening 12 is illustrated as having a circular shape, it should be understood that a variety of different shaped openings such as oval, square, random, non-geometric shape and the like may be utilized. In an embodiment of the present invention, the device 10 is portable, disposable, and customizable. The device 10 can be used in connection with irregular areas of the human body.

The device 10 includes a seal 14 surrounding the opening 12 that is optionally used to removably attach the device 10 to a patient. Further, device 10 includes one or more conduits 16 (two illustrated) that have passageways in fluid communication with chamber 11. The conduits 16 provide fluid communication with a treatment gas device (not shown) that supplies the treatment gas to the device 10. Treatment gas, for example, oxygen, can be introduced into chamber 11 via one of the conduits, and then withdrawn out of the chamber using the other conduit. This allows for the continuous flow of treatment gas into and out of the chamber 11. A single conduit 16 can be used for non-continuous or sequential treatment gas flow.

As best seen in FIG. 2, device 10 includes a top sheet 18 and a bottom sheet 20 joined together to form an enclosure having an interior defining the treatment chamber 11. The top and bottom sheets, 18 and 20, are connected to each other at or adjacent their respective outer edges, for example, by radio frequency ("RF") welding, heat sealing, or the like, to form the outer perimeter or edge 22 of device 10. The sheets may be provided by separate sheets, or may be formed from a single sheet that is folded over onto itself, with three sides welded together, and the fourth side optionally also welded to form a seam, for example. The sheets may be single-ply or multi-ply sheets generally of synthetic polymer material which is preferably thermoplastic in nature to allow for heat setting or RF welding.

The seal 14 according to one embodiment includes laminated overlying layers that include a first adhesive layer 24, a foam layer 26, a second adhesive layer 28 and a releasable tape seal 30. The tape seal 30 prevents the second adhesive layer 28 from becoming contaminated or attaching to an object before the clinician is ready to attach the device 10 to the patient.

The first adhesive layer 24 attaches the foam layer 26 to the top sheet 18 surrounding opening 12. The second adhesive 28 attaches the foam layer 26 to a patient once the tape seal 30 is removed. The foam layer 26 is preferably a closed cell foam material optionally an open cell foam material affixed to the top sheet 18 using the first adhesive layer 24. Alternately, foam layer 26 may be welded, such as by heat welding directly to sheet 18. Ideally, the connection between the foam layer 26 and the top sheet 18 is stronger than the connection between the foam layer 26 and the patient, so that when the device 10 is removed, the seal 14 will be removed along with the device 10. It is also contemplated that the adhesive layers 24, 28 can be eliminated by using a compliant layer 26 having adhesive properties.

The tape seal 30 is removed before use, and the opening 12 of the device 10 is placed over a wound on the patient. When placed over the wound, the top sheet 18 is located adjacent the patient's skin. Pressure is applied to the bottom sheet 20, optionally at the portion of the bottom sheet that is aligned with seal 14, so that second adhesive layer 28 affixes to the patient's skin to form a seal around the wound. The second adhesive layer 28 and the foam layer 26 form a seal, such as a hermetic seal, against the patient's skin. Once seal 14 is attached to the patient, the device forms a closed chamber 11 whereby treatment gas can enter the device 10 and treat the wound. The conduits 16 may be coupled to the gas treatment device before or after the device 10 is placed over the wound. Once conduits 16 are attached to a gas treatment device which supplies treatment gas to conduits 16, treatment may be commenced.

In an embodiment of the present invention, the seal 14 spans a large surface area of the top sheet 18. Although shown as a circular ring, the seal 14 may be configured in any shape or size. The seal 14 as thus far described will accommodate wounds up to a predetermined size. In order to adjust the size of opening 12 to accommodate different size wounds, the seal and the top sheet 18 have a plurality of concentric weakened regions that permit corresponding portions of the seal 14 and of the top sheet 18 to be removed without the need for a tool.

Figure 3A:
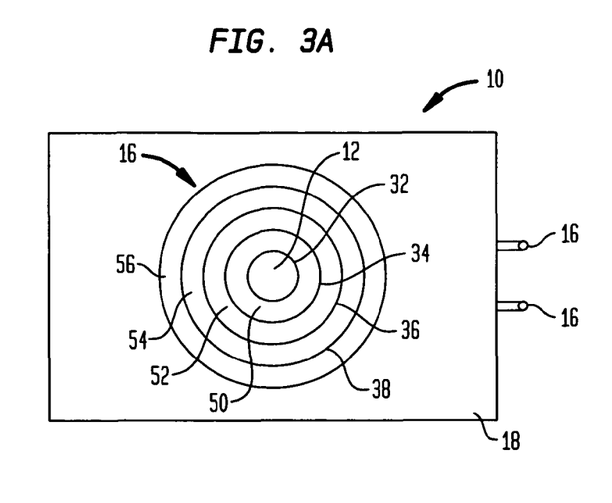
FIG. 3A is a top plan view of the device of FIG. 1.

In the illustrated embodiment, seal 14 and opening 12 each have a circular shape, and the weakened areas or regions are in the form of a variety of concentric circular weakened regions 34, 36 and 38 providing three removable seal regions 50, 52, 54, and 56, as shown in FIG. 3A. In the illustrated embodiment, the weakened areas are in the form of tear lines. It should be understood that the weakened regions can be formed at varying distances from the center of the opening 12 and may vary in shape or size as well. Generally, the tear lines are formed at uniformly increasing distances around the opening 12; though, it should be understood that the location of the tear lines may be varied.

In the illustrated embodiment of the present invention, the opening 12 is about four inches in diameter surrounded by seal region 50. The first tear line 34 can be formed, for example, at a diameter of six inches; the second tear line 36 can be formed, for example, at a diameter of eight inches; and the third tear line 38 can be formed, for example, at a diameter of ten inches. Although diameters of six, eight and ten inches are disclosed herein, the number of tear lines and the variety of size ranges can vary depending upon the size of the device 10. These tear lines allow the clinician to simply tear out the seal 14 and corresponding portion of sheet 18 to a desired size. Thus, if a clinician desired a six-inch opening, they would tear out the seal 14 at the tear line 34 (seal region 50), leaving behind a six-inch diameter opening to encircle the wound.

Figure 3B:
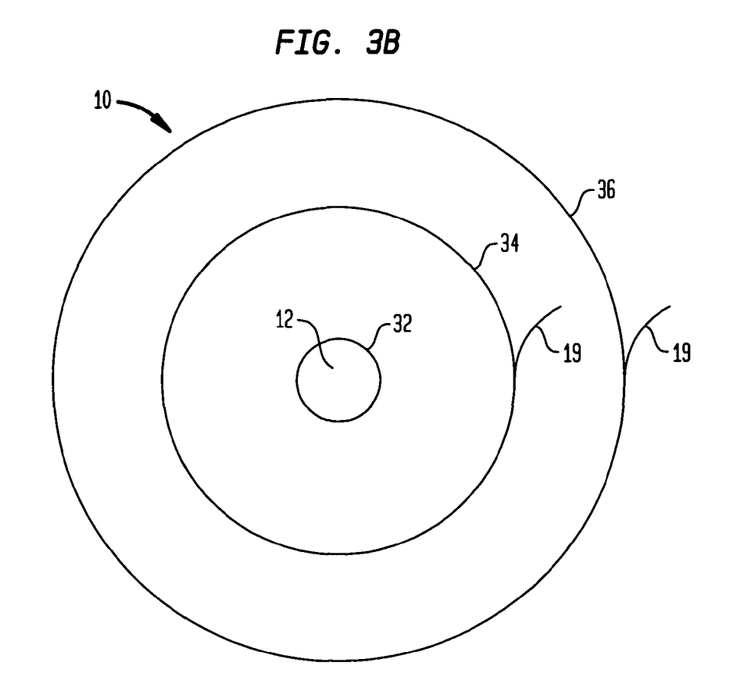
FIG. 3B is a detailed enlarged plan view of a portion of the device of FIG. 3A.

The tear lines forming the opening 12 can be made in the device 10 in several ways. First, the foam layer 26, the tape seal 30, and the top sheet 18 may be perforated in a conventional manner using a die. Second, a method using a similar RF welding/bar seal process that can seal the top sheet 18 to the bottom sheet 20 may be used. The foam layer 26 and the tape seal 30 are perforated while the top sheet 18 is weakened at appropriate areas, such that these layers may be easily torn. As shown in FIG. 3B, a kiss cut may be incorporated. The kiss cut utilizes a string or tape 19 that encircles the foam layer 26 at perforations in the foam layer 26 and at weakened locations in the top sheet 18, allowing the clinician to pull on the string 19 and tear the seal 14.

Figure 4:
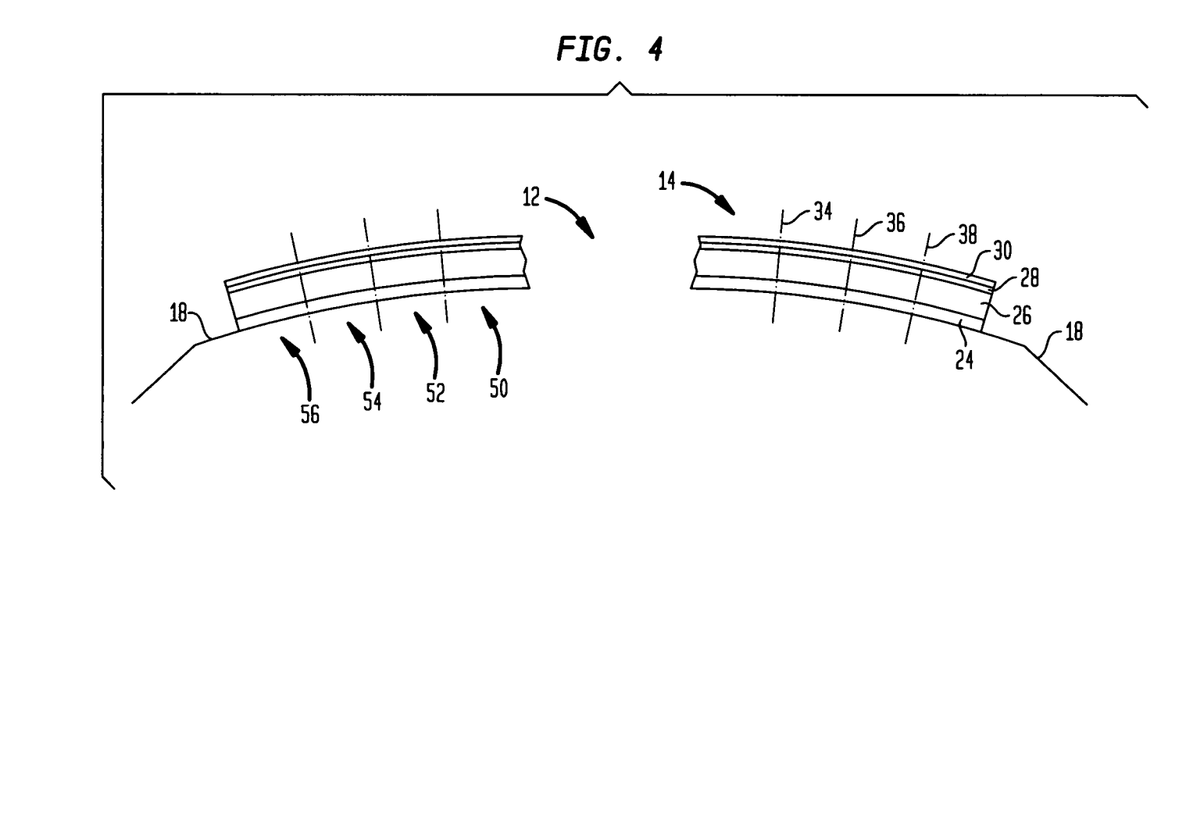
FIG. 4 is a cross-sectional view of a seal according to an embodiment of the present invention.

The tear lines are shown in greater detail in FIG. 4 in accordance with one embodiment. As noted, tear lines indicated by cut lines 34, 36 and 38 can go through the entire seal 14 and can also penetrate the top sheet 18 at spaced concentric locations, so that a portion of the top sheet 18 is also torn when the seal 14 is torn.

Figure 5A:
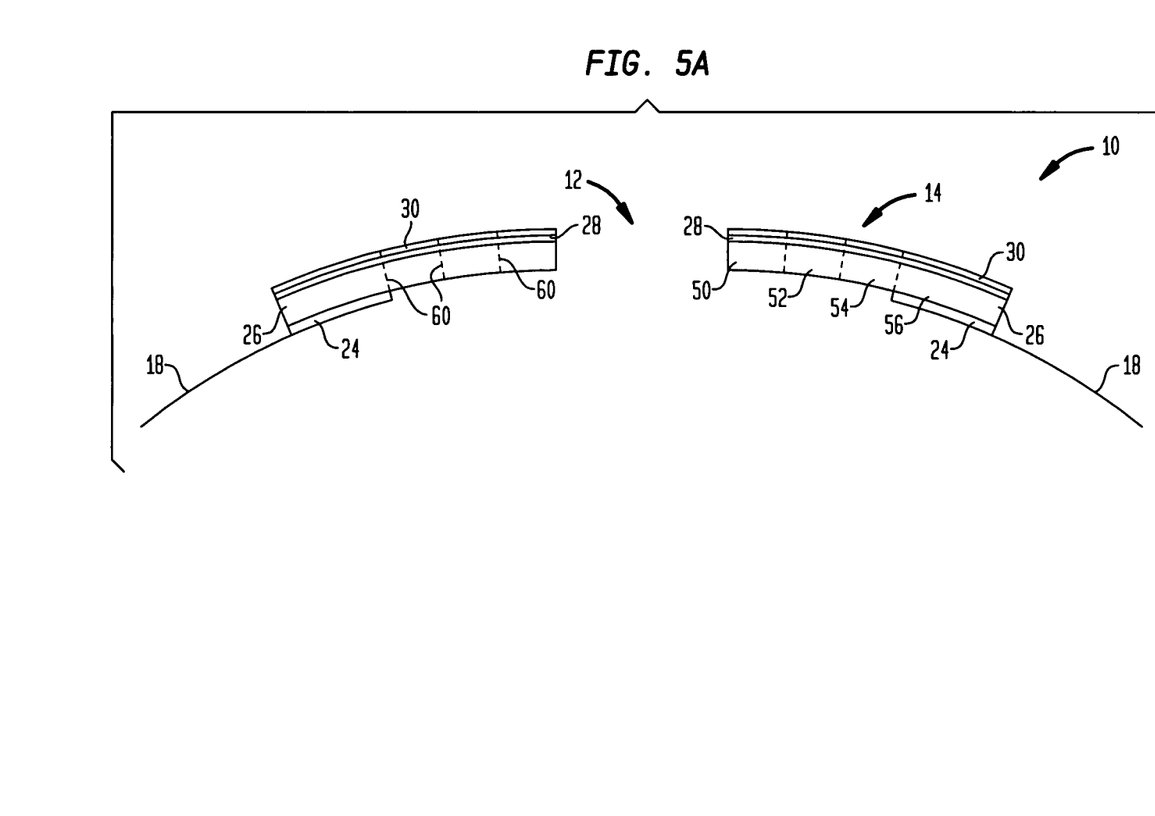
FIGS. 5a and 5b are cross-sectional views of a seal according to two embodiments of the present invention.

FIG. 5 discloses another embodiment of the present invention. As shown, the device 10 has a top sheet 18 provided with an enlarged opening 12. The seal 14 is attached to the top sheet 18 about an outer peripheral portion of the seal by the adhesive layer 24. As a result, the seal regions 50, 52, 54 defined by the weakened regions 60 are not attached or supported by the top sheet 18. This construction eliminates providing weakened regions in the top sheet 18 which coincides with the weakened regions 60 in the seal 14. In this configuration, the seal 14, along with the weakened regions and cut lines 34, 36, and 38 may be pre-formed and then attached to the top sheet 18 at the enlarged opening 12 of the top sheet 18. In pre-forming the seal 14, it is possible to leave an opening of the seal intact, such that the seal 14 has no opening. In such a case, the clinician can use a first tear line at line 32 to create the initial opening.

Similarly, in the embodiment where the seal 14 is attached to the top sheet 18 and the tear lines are formed on the top sheet 18 and the seal 14 simultaneously, tear line 32 can be formed, leaving the opening intact. Thus, the clinician can create the opening 12 by pulling at the tear line 32. Therefore, in either method of forming this device, the opening 12 itself can be torn out by the clinician; the device 10 would not initially include an opening.

Figure 5B:
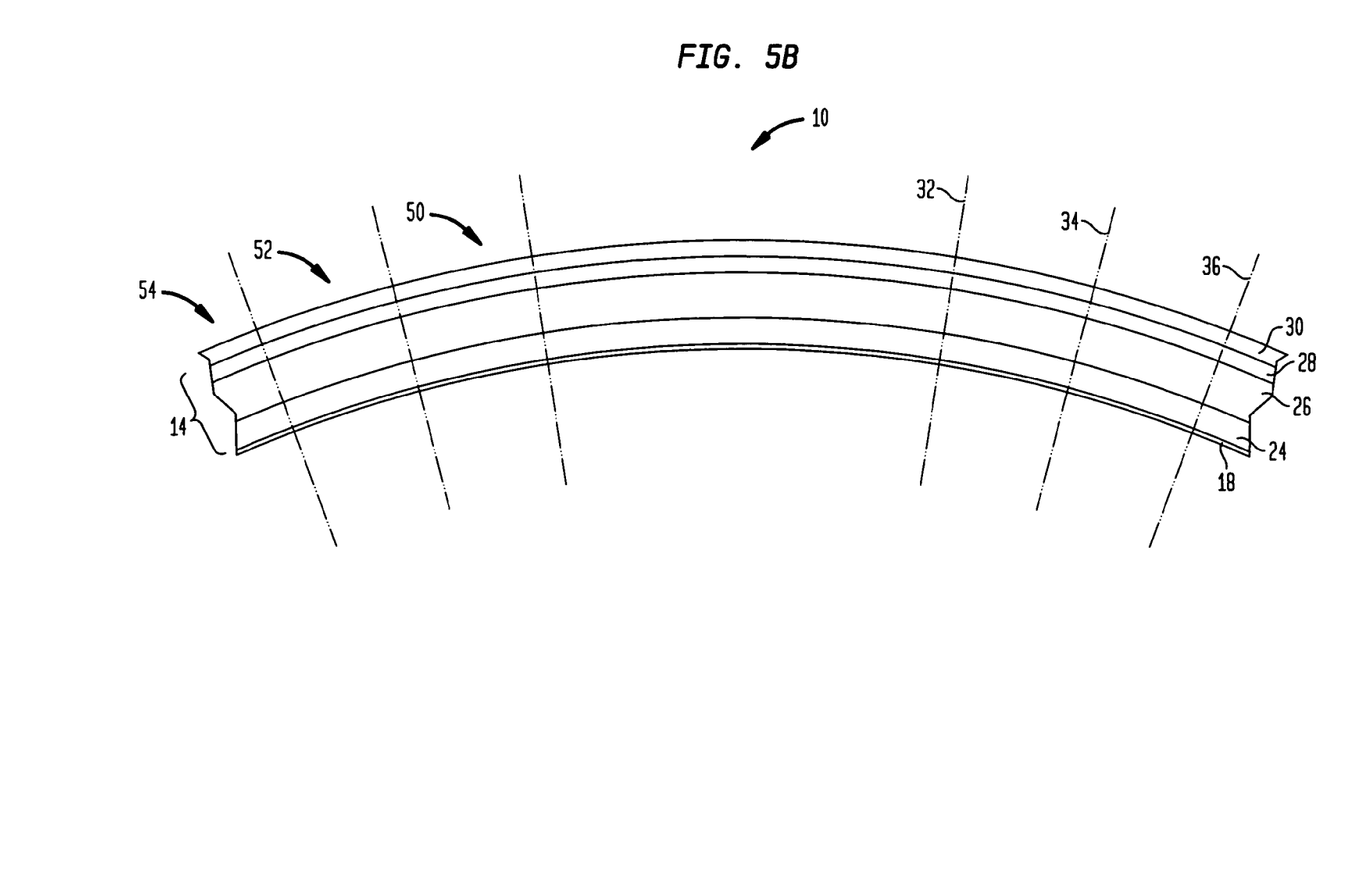

In yet another embodiment of the present invention, the top sheet 18 need not include an opening prior to it being attached to the seal 14. In this example, the seal 14 can overlie an entire area of the top sheet 18, or a substantial part thereof. Then tear lines can be formed. Thus, when a clinician removes a particular weakened region, corresponding portions of both the seal 14 and the top coat 18 are removed. In this example, the opening 12 does not already exist on the top sheet 18 and is created by the clinician customizing the opening. With reference to FIG. 5b, the layers of the seal 14, overlie the top sheet 18 that contains no initial opening. A tear line 32 can be created having a predetermined size. Tear lines 34, 36 can be created as previously discussed. Thus, when the clinician pulls at tear line 32, for example, opening 12 will be created at this point. Then the seal 14 and top sheet can be affixed to each other.

Figure 6:
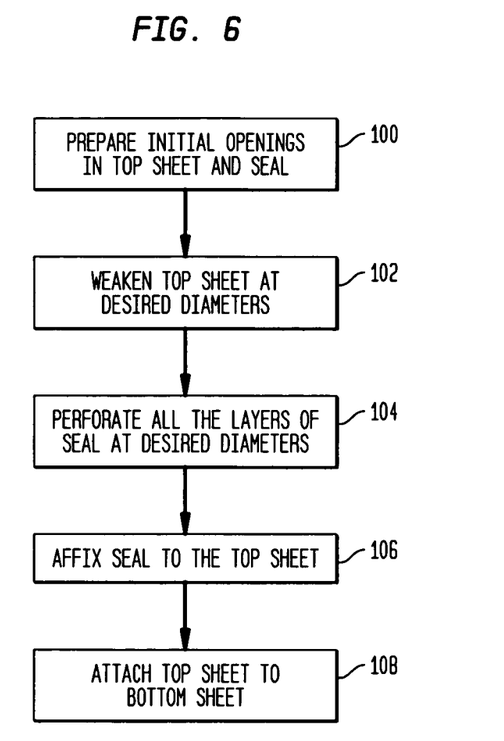
FIG. 6 is a flow diagram of one method of forming the device of FIG. 1 in an embodiment of the present invention.

FIG. 6 is a flow diagram of a method of forming the tear lines at the openings in the device 10. First, at step 100, the initial opening 12 in the top sheet 18 and seal 14 are formed. The initial opening in one embodiment of the present invention can begin at about two inches in diameter and may be cut in the conventional manner using a die. The seal 14 and the top sheet 18 are preferably cut separately and can be cut at various locations remote from each other. Thereafter, at step 102, the top sheet 18 is weakened at the desired diameters at various locations along those diameters. For instance, the circumferential weakening may be utilized at diameters between about six and ten inches for the embodiment described with reference to FIG. 4.

Thereafter, at step 104, all of the layers of the seal are perforated using a die or the like. Once again, all of the layers of the seal 14 are perforated in an embodiment of the present invention at diameters of about six, eight and ten inches. At step 106, the seal 14 is affixed to the top sheet 18 using the first adhesive layer 24. A step 108, the top sheet 18 is affixed to the bottom sheet 20. Preferably, the top sheet 18 and the bottom sheet 20 are formed of a polymer material, such as vinyl, and may be welded together. Although other suitable materials may be utilized, preferred materials are heat sealable. Once welded, the top sheet 18 and the bottom sheet 20 are cut by a die in the shape of the device 10. As stated previously, any shape can be utilized. The welding of the top and bottom sheets, 18 and 20, respectively, may be done using RF welding or heat sealing or the like, such as disclosed in U.S. Pat. No. 5,154,697, which is hereby incorporated by reference.

Figure 7:
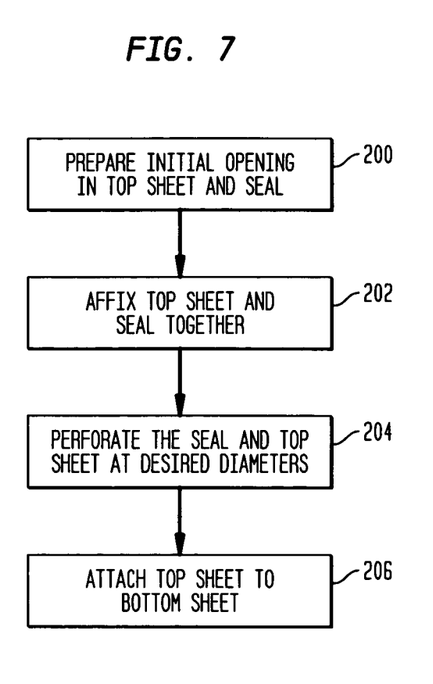
FIG. 7 is a flow diagram of another method of forming the device of FIG. 1 in another embodiment of the present invention.

In another embodiment of the present invention, FIG. 7 illustrates a second method of forming the customizable opening in the device 10. As in step 100, the initial opening 12 is formed in the top sheet 18, and in the seal 14 at step 200. Once again, these openings can be any size, such as two inches in diameter, and can be performed at various locations that are remote from each other. Next, at step 202, the top sheet 18 and the seal 14 are affixed together using the first adhesive layer 24. Thereafter, at step 204, the seal 14 and the top sheet 18 are perforated at desired diameters. Once again, the diameters or distances from the initial opening can vary.

Thereafter, the top sheet 18 and the bottom sheet 20 are welded together and then cut in the shape of the device 10.

Figure 8:
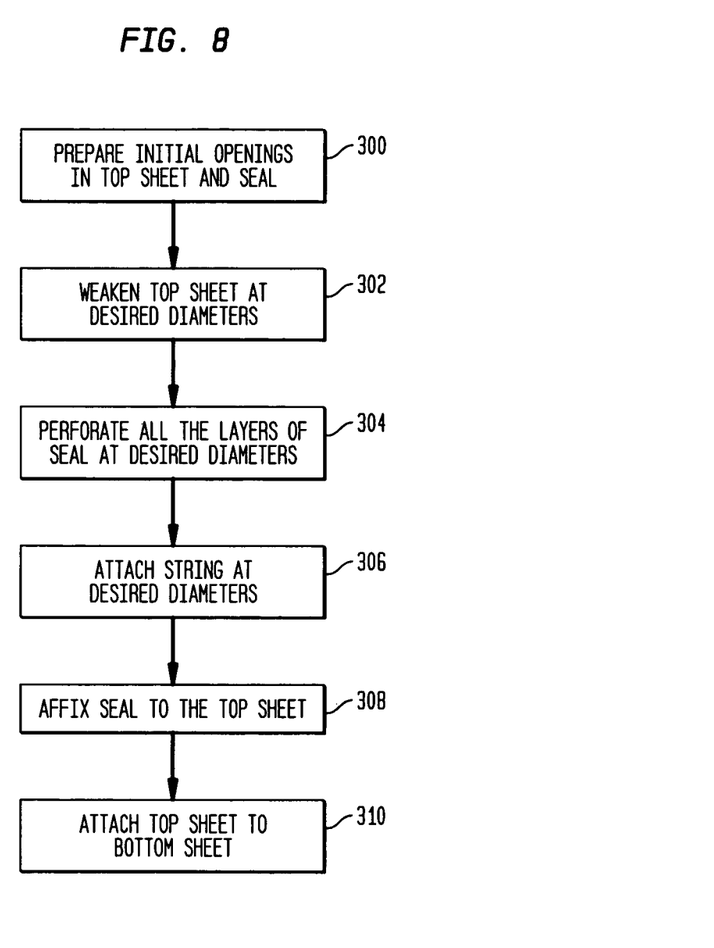
FIG. 8 is a flow diagram of a third method of forming the device of FIG. 1 in yet another embodiment of the present invention.

Another embodiment of the present invention is depicted in FIG. 8 wherein, at step 300, the initial openings 12 are formed in the top sheet 18 and the seal 14. Next, at step 302, the top sheet 18 is weakened at desired diameters as mentioned previously. Thereafter, at step 304, all of the layers of the seal 14 are perforated at the desired locations. Then at step 306, a string is attached at the various locations on the seal. Any manner of attachment may be utilized. Then, at step 308, the seal 14 is affixed to the top sheet 18 using the first adhesive layer 24. Finally, the top sheet 18 is attached to the bottom sheet 20 using welding and is then cut in the shape of the device 10.

In a preferred embodiment of the present invention, the foam layer is formed of a 3M™ white polyethylene foam single-coated medical tape, available from 3M™ Corporation, of St. Paul, Minn.

Once the foam layer 26 has been torn to the desired opening, the inherent properties of the type of material used for the foam layer 26 and its memory allow the foam layer 26 to reform itself and close around any remaining perforations, preventing leakage of the treatment gas through the perforations. Because of the flexibility of and adhesive characteristics imparted to the foam layer 26, it may be easily affixed to any location on a patient, including such awkward areas as the knee or ankle. The intrinsic nature of the foam layer 26 allows the foam layer 26 to expand and cover over the perforations and still provide a hermetic seal that prevents the treatment gas from leaking.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A hyperbaric wound treatment device comprising:
   an enclosure defining an interior region providing a wound treatment chamber, said enclosure comprising first and second polymer sheets attached to each other about their respective edges;
   a first circular line of perforations within said first sheet;
   a second circular line of perforations within said first sheet arranged concentric with said first line of perforations outwardly thereof forming an annular region of said first sheet therebetween;
   a first seal adhered to said first sheet radially inward of said first circular line of perforations;
   a second seal adhered to said annular region of said first sheet and bound by said first and second circular lines of perforations, said first seal separable from said second seal;
   said first and second seals each comprising a foam body having opposing first and second sides, a first adhesive layer adhered to said first side, a second adhesive layer adhered to said second side, and a release layer releasably adhered to said first adhesive layer, said first and second seals adhered to said first sheet by said second adhesive layer;
   said first seal and an adhered portion of said first sheet adapted to be torn away together from a remainder of the first sheet along said first circular line of perforations;
   said second seal and an adhered annular region of said first sheet adapted to be torn away together from a remainder of the first sheet together with the first seal and the adhered thereto portion of the first sheet along said second circular line of perforations;

a fluid inlet in communication with said wound treatment chamber for supply of a treatment medium thereto; and a fluid outlet in communication with said wound treatment chamber for withdrawal of the treatment medium therefrom.

2. The wound treatment device of claim 1, wherein said first and second sheets are flat.

3. The wound treatment device of claim 1, further including a third circular line of perforation concentric with and radially inward of said first circular line of perforations, wherein said first sheet radially inward of said first seal is removable along said third circular line of perforations, thereby forming an opening in communication with said treatment chamber.

4. The wound treatment device of claim 1, wherein said first sheet includes an opening in communication with said treatment chamber radially inward of said first seal.

5. The wound treatment device of claim 1, further including a third seal adhered to said first sheet radially outward of said second line of perforations.

6. The wound treatment device of claim 1, wherein said first seal is separable from said second seal by a weakened region therebetween.

7. The wound treatment device of claim 6, wherein the weakened region comprises a plurality of perforations.

8. The wound treatment device of claim 6, wherein the weakened region comprises a tear line.

9. The wound treatment device of claim 6, wherein the weakened region comprises a cut line.

* * * * *